United States Patent [19]
Rhodes

[11] Patent Number: 5,665,117
[45] Date of Patent: Sep. 9, 1997

[54] ENDOVASCULAR PROSTHESIS WITH IMPROVED SEALING MEANS FOR ANEURYSMAL ARTERIAL DISEASE AND METHOD OF USE

[76] Inventor: Valentine J. Rhodes, 608 Winding River Rd., Bricktown, N.J. 08723

[21] Appl. No.: 620,072

[22] Filed: Mar. 21, 1996

Related U.S. Application Data

[63] Continuation-in-part of Ser. No. 562,768, Nov. 27, 1995, abandoned.

[51] Int. Cl.⁶ .................................................. A61F 2/04
[52] U.S. Cl. .......................... 623/1; 623/12; 606/192; 606/194; 606/195; 606/198
[58] Field of Search ........................ 623/1, 11, 12; 606/190–200

[56] References Cited

U.S. PATENT DOCUMENTS

| | | |
|---|---|---|
| 4,562,596 | 1/1986 | Kornberg . |
| 5,122,154 | 6/1992 | Rhodes . |
| 5,156,620 | 10/1992 | Pigott ............................... 623/1 |
| 5,207,695 | 5/1993 | Trout, III . |
| 5,211,658 | 5/1993 | Clouse . |
| 5,275,622 | 1/1994 | Lazarus et al. . |
| 5,282,824 | 2/1994 | Gianturco . |
| 5,316,023 | 5/1994 | Palmaz et al. . |
| 5,330,528 | 7/1994 | Lazim . |
| 5,360,443 | 11/1994 | Barone et al. . |
| 5,370,691 | 12/1994 | Samson . |
| 5,387,235 | 2/1995 | Chuter . |
| 5,405,379 | 4/1995 | Lane . |
| 5,464,419 | 11/1995 | Glastra ............................... 606/194 |

*Primary Examiner*—John G. Weiss
*Assistant Examiner*—John M. Black
*Attorney, Agent, or Firm*—Caesar, Rivise, Bernstein, Cohen & Pokotilow, Ltd.

[57] ABSTRACT

An intraluminal prosthesis for use in a blood vessel, e.g., the abdominal aorta, at which an aneurysm defining an aneurysmal space is located. The prosthesis basically comprises an expandable sleeve, an outer balloon, a pair of sealing rings or a sealing cover, a pair of expandable anchoring stents, and plural expandable support stents. The sleeve is an elongated tubular member defining a passageway having a pair of open ends for conveying blood therethrough. The outer balloon is disposed about the sleeve and is arranged to be filled with a fluid, e.g., a gel or saline, to cause it to extend outward to fill the aneurysmal space. The sleeve is arranged to be expanded and held in that state by the stents. The anchoring stents fixedly secure the prosthesis to the interior of the vessel, with the ends of the sleeve being sealed by the sealing rings or sealing cover to portions of the vessel on respective sides of the aneurysm to preclude the ingress of blood between the outer balloon and the interior of the vessel at the aneurysm, while the blood is conveyed through the passageway, and to preclude the egress of material, e.g., an embolus, from between the outer balloon and the interior of the vessel at the situs of the aneurysm.

13 Claims, 9 Drawing Sheets

ENDOVASCULAR PROSTHESIS WITH IMPROVED SEALING MEANS FOR ANEURYSMAL ARTERIAL DISEASE AND METHOD OF USE

This application is a CIP of case 08/562,768, filed Nov. 27, 1995 now abandoned.

BACKGROUND OF THE INVENTION

The invention of this application relates generally to medical devices and methods of use in vessels, ducts or lumens of living beings, and more particularly to expandable prostheses and methods of use for the treatment of aneurysmal arterial disease.

The use of an intraluminal endovascular prosthesis for the treatment of aneurysmal arterial disease, e.g., an abdominal aortic aneurysm, has been attempted experimentally as an alternative to conventional vascular surgery. That experimentation involved the insertion into a blood vessel of a tubular prosthetic graft via the open insertion through a short segment exposed portion of the blood vessel.

Prior art experimentations have been fraught with failures and difficulties owing to various factors. In particular, the factors which must be addressed for adequate placement of the prosthesis, particularly if it is to be placed by percutaneous introduction from a remote site, (e.g., percutaneous introduction into the femoral artery), followed by passage through portions of the vascular system to the situs of the aneurysm (a desirable mode of introduction vis-a-vis direct arterial cut-down) are as follows. The graft should exhibit the ability to pass through a percutaneous sheath of reasonable size for passage to the arterial aneurysm. The graft should be able to pass through the aneurysm thrombus without dislodging emboli. These first two factors necessitate that the prosthesis be very small, (i.e., have a very small "crossing diameter"). The prosthesis should also be very flexible to pass over a guide wire or similar apparatus the enable it to be threaded or passed through a redundant, kink and potentially stenotic arteries to reach the aneurysm, without exhibiting a high risk of damaging those vessels. Typically with aortic aneurysms there is very little vascular tissue available to anchor the prosthesis sufficiently proximally, and to anchor and seal the prosthesis to the arterial wall to prevent leakage and/or migration of the prosthesis. Thus, the prosthesis should be constructed so that it can be readily secured in place within the aneurysmal space in the vessel so that it is resistant to migration. In addition the prosthesis must be sealed sufficiently to the arterial wall on the proximal and distal sides of the aneurysm prevent the ingress of blood into the interface between the prosthesis and the arterial wall to prevent emboli from being dislodged and freed to flow into the distal vascular system. Lastly, the prosthesis should be constructed so that it provides a passageway or lumen of sufficient diameter for blood to flow freely therethrough, while preventing subsequent rupturing of the aneurysm.

Heretofore the prior art has not provided any prosthesis and/or method of use which adequately addresses the above factors.

The following United States Letters patents have disclosed devices for the treatment of aneurysmal arterial disease: U.S. Pat. No. 4,562,596 (Kornberg); U.S. Pat. No. 5,207,695 (Trout III); U.S. Pat. No. 5,211,658 (Clouse); U.S. Pat. No. 5,275,622 (Lazarus et al.); U.S. Pat. No. 5,282,824 (Gianturco); U.S. Pat. No. 5,316,023 (Palmaz et al.); U.S. Pat. No. 5,330,528 (Lazim); U.S. Pat. No. 5,360,443 (Mazza et al.); U.S. Pat. No. 5,370,691 (Samson); U.S. Pat. No. 5,387,235 (Chuter); and U.S. Pat. No. 5,405,379 (Lane).

Accordingly, the need exists for apparatus and methods for effectively treating aneurysmal arterial disease.

In my U.S. Pat. No. 5,122,154, whose disclosure is incorporated by reference herein, there is disclosed an intraluminal bypass graft for revascularization of occluded arteries. That bypass graft is arranged for placement in a blood vessel, duct, or lumen, to hold it open and comprises a sleeve having plural stents secured to it at spaced locations therealong. The sleeve is an elongated tubular member formed of a conventional graft material which is flexible and impervious to the ingrowth of tissue. Each stent is a generally ring-like member formed a plurality of interconnected movable links and is mounted about the periphery of either the inner or outer surface, of the sleeve at selected points along the sleeve to form respective spaced first sleeve sections. Each of the first sections extends for only a portion of the length of the graft, thereby leaving a plurality of second sleeve sections interposed between the first sleeve sections. The stents and the sleeve are arranged to be expanded, by any suitable means, e.g., a balloon catheter, from a compact state to an expanded state to increase the inner cross sectional area diameter of the sleeve. In the expanded state the stents are resistant to contraction back to the compact state. The graft is able to bend with respect to its longitudinal axis to enable it to be readily accommodated within a curved blood vessel, duct, or lumen.

I have determined that the bypass graft of my above mentioned patent (or even portions of it), can be used to form a portion of a prosthesis of this invention. That prosthesis has the ability: to traverse tortuous or stenosed paths to the situs of the aneurysm without risk of damage to the vessel being traversed or dislodging a emboli; to remain permanently anchored in place against migration, while sealing and trapping any blood clot in the aneurysmal space between it and the arterial wall to prevent the egress of emboli therefrom; to prevent rupture of the aneurysm; and to provide for adequate blood flow through it.

In my aforementioned patent application Ser. No. 08/562, 728 there is disclosed and claimed an intraluminal prosthesis for aneurysmal arterial disease which overcomes many of the disadvantages of the prior art.

OBJECTS OF THE INVENTION

It is a general object of this invention to provide an expandable intraluminal prosthesis and method of use of the same which also overcomes many of the disadvantages of the prior art.

It is a further object of this invention to provide an expandable intraluminal prosthesis and method of use for which has the ability to be introduced either percutaneously or through arterial cut-down, and which is easy to use.

It is a further object of this invention to provide an expandable intraluminal prosthesis and method of use for aneurysmal arterial disease which has the ability to be introduced either percutaneously or through arterial cut-down to traverse tortuous or stenosed paths to the situs of the aneurysm without risk of damage to the vessel being traversed.

It is a further object of this invention to provide an expandable intraluminal prosthesis and method of use for aneurysmal arterial disease which has the ability to be introduced either percutaneously or through arterial cut-down to traverse tortuous or stenosed paths to the situs of the aneurysm without risk of dislodging emboli.

It is still a further object of this invention to provide an expandable intraluminal prosthesis and method of use for aneurysmal arterial disease which has the ability to be introduced either percutaneously or through arterial cutdown and which when positioned has the ability to remain permanently anchored in place.

It is yet a further object of this invention to provide an expandable intraluminal prosthesis and method of use for aneurysmal arterial disease which has the ability to be introduced either percutaneously or through arterial cutdown and which reduces the risk of blood leakage into the aneurysmal space and its attendant risk of aneurysm growth and/or rupture.

SUMMARY OF THE INVENTION

These and other objects of this invention are achieved by providing a prosthesis for the treatment of aneurysmal disease and a method of use of the prosthesis. The prosthesis is arranged for introduction within a portion of a blood vessel, duct or lumen, e.g., the abdominal aorta, of a living being having an aneurysm in the wall.

The prosthesis basically comprises sleeve means, outer balloon means, and sealing means. The sleeve means comprises an elongated tubular sleeve defining a passageway therethrough. The passageway has a longitudinal axis and a pair of open ends and is arranged to convey fluid, e.g., blood, therethrough. The outer balloon means is disposed about said sleeve means and is arranged to be filled with a filling material, e.g., a gel or saline solution.

The prosthesis is arranged to be fixedly secured to the interior of the blood vessel, with the ends of the sleeve means being sealed to portions thereof on respective sides of the aneurysm to preclude the ingress of fluid, e.g., blood, between the outer balloon means and the interior of the vessel, while enabling fluid, e.g., blood, to be conveyed through the passageway, and to preclude the egress of material, e.g., an embolus, from between the outer balloon means and the interior of the vessel at the situs of the aneurysm.

The sealing of the ends of the sleeve means to the interior of the vessel is accomplished in a preferred embodiment by sealing means in the form of a covering, e.g., a mesh-like material, extending over most of the outer surface of the balloon means so that portions of the covering are located adjacent the ends of the sleeve means. The covering also serves to occlude, block, or otherwise impede or reduce the leakage of blood from one or more collateral branch arteries into the aneurysmal space.

In accordance with one preferred embodiment of the prosthesis, the sleeve means is expandable to an expanded state when in position, and is held in the expanded state by plural stents. Some of the stents serve to anchor the prosthesis in place and make use of plural projections arranged for engagement with the interior of the wall of the vessel. The projections constitute another invention of mine which is the subject of a copending patent application, Ser. No. 08/562,727, filed on Nov. 27, 1995, entitled Endovascular Stent With Secure Mounting Means and whose disclosure is also incorporated by reference herein.

DESCRIPTION OF THE DRAWINGS

Other objects and many attendant advantages of this invention will become readily appreciated as the same becomes better understood by reference to the following detailed description when considered in connection with the accompanying drawings wherein.

DETAILED DESCRIPTION OF THE PREFERRED EMBODIMENTS

Figure 1:
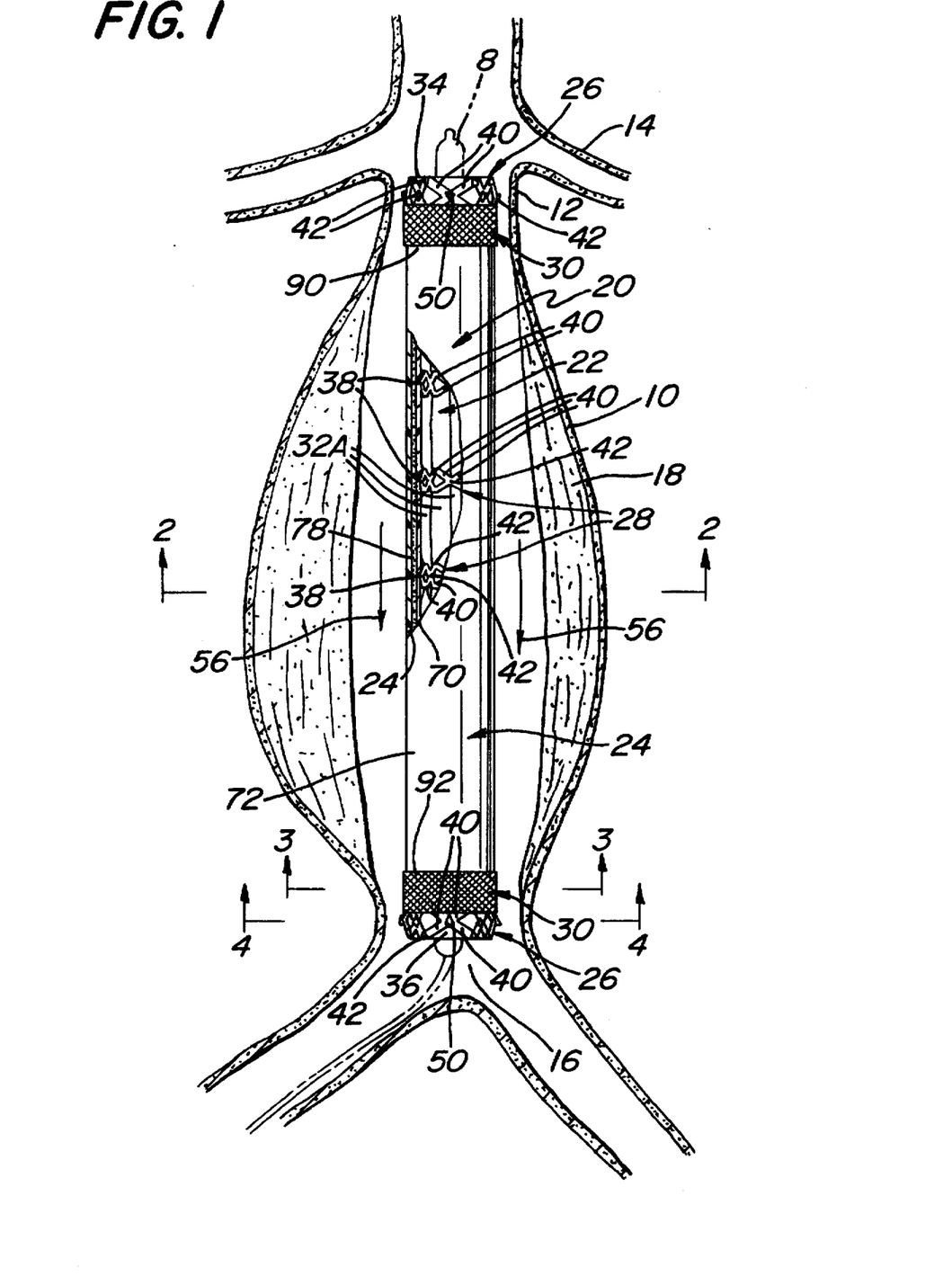
FIG. 1 is a front plan view illustration of a portion of the abdominal aorta of a living being showing the prosthesis of the subject invention in partial section located therein, with the prosthesis being in its compact state.

Referring now to various figures of the drawing where like reference numerals refer to like parts there is shown at 20 in FIG. 1 an expandable, intraluminal prosthesis constructed in accordance with this invention.

The prosthesis 20 is arranged for introduction within a portion of a blood vessel, duct or lumen of a living being having an aneurysm in its wall to prevent further expansion or rupture of the aneurysm, while providing for patency of the vessel, duct, or lumen in which the aneurysm is located. One particularly significant application of the subject invention is the treatment of aneurysmal arterial disease, e.g., the treatment of an abdominal aortic aneurysm. That aneurysm is shown in FIG. 1 and is designated by the reference numeral 10. As can be seen therein the aneurysm 10 extends for a substantial portion of the abdominal aorta 12, between the renal arteries 14 and the bifurcation 16 of the iliac arteries. As is typical a thrombus 18 is attached to the inner wall of the artery in the aneurysmal space.

The prosthesis 20 of this invention is suitable for placement within the aneurysmal space in the abdominal aorta 12 by either conventional "cut-down" surgical techniques, or by percutaneous placement. Depending upon the condition of the patient's vascular system, percutaneous placement of the device 20 may be effected by introducing the prosthesis at one puncture situs, e.g., a puncture in the femoral artery, followed by threading or passing the prosthesis through appropriate connecting portions of the vascular system to the situs of the aneurysm 10. In either type of introduction, e.g., arterial cut-down, or percutaneous, the prosthesis 20 is arranged to be initially maintained in a compact or compressed state (as shown in FIG. 1) to facilitate its placement into the aneurysmal space. Once in that space it is arranged to be expanded so that it becomes anchored in place to seal the thrombus 18 between it and the interior wall of the aorta, while providing a passageway through it for blood to flow freely.

Figure 2:
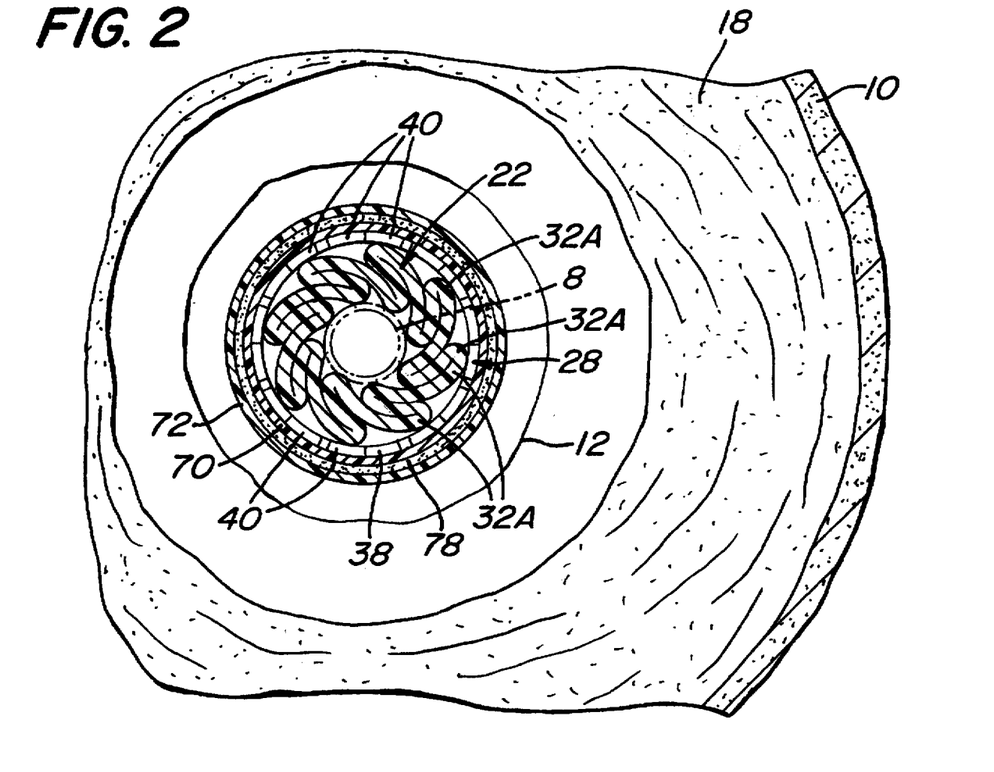
FIG. 2 is an enlarged sectional view taken along line 2—2 of FIG. 1.
Figure 3:
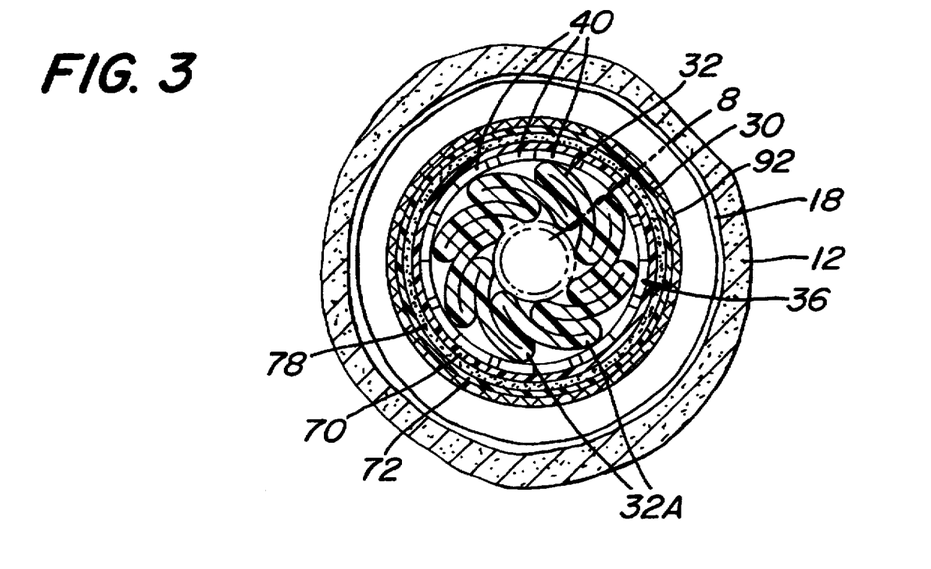
FIG. 3 is an enlarged sectional view taken along line 3—3 of FIG. 1.

Referring now to FIG. 1 it can be seen that the prosthesis 20 is in its compact state within the abdominal aorta 12 at the location of the aneurysm 10. As will be described in considerable detail later, the expansion of the prosthesis 20 from its compacted state shown in FIG. 1 to its expanded state shown in FIG. 2 is preferably accomplished by a conventional balloon catheter shown by the phantom lines in FIGS. 1 and 5. However, any other suitable expansion device or instrument, e.g., a mandrel (not shown), may be used for that purpose.

The prosthesis 20 basically comprises sleeve means 22, outer balloon means 24, anchoring stent means 26, plural intermediate support stent means 28, and sealing means 30. The sleeve means comprises an elongated tubular sleeve member 32 having a pair of open ends with a central passageway extending therebetween. The tubular sleeve member 32 is formed of a thin and highly flexible material, such as expanded polytetrafluoroethylene, used for conventional vascular grafts. Examples of such prior art graft materials are those sold by W. C. Gore and Company under the trademark GORTEX or those sold by Impra Inc. under the trademark IMPRAGRAFT. The sleeve member 32 is configured so that it is pleated, i.e., it includes a plurality of longitudinally extending pleats 32A. Each of the pleats extends the entire length of the sleeve 32. The pleated sleeve is normally in a compacted state as shown in FIG. 1, that is each of the pleats overlies and abuts a contiguous portion of an immediately adjacent pleat.

Figure 6:
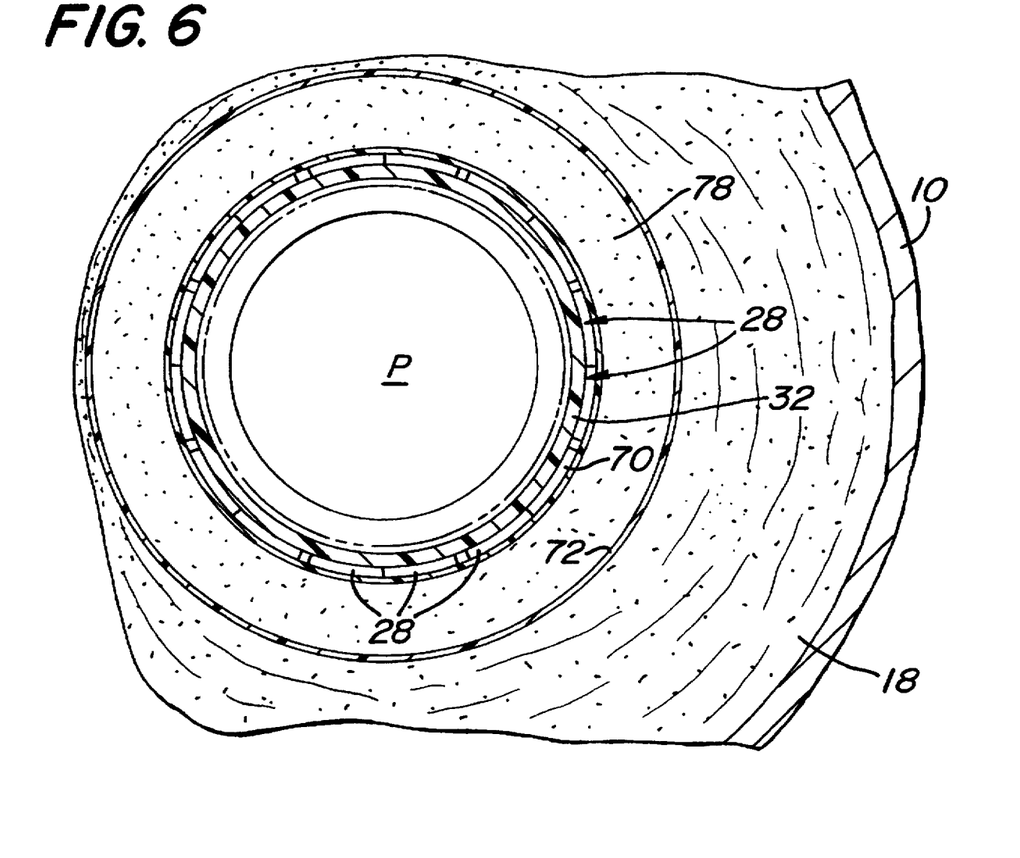
FIG. 6 is an enlarged sectional view taken along line 6—6 of FIG. 5.
Figure 7:
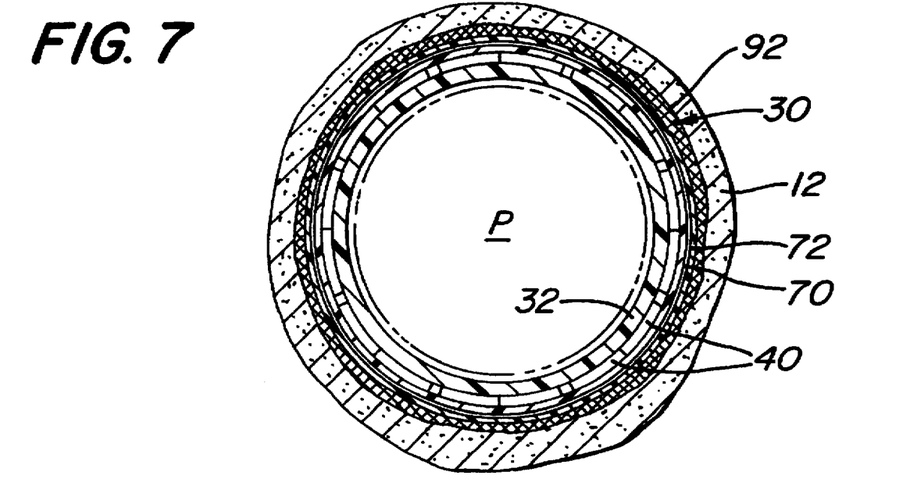
FIG. 7 is an enlarged sectional view taken along line 7—7 of FIG. 5.

The sleeve member 32 is arranged to be expanded to a maximum expanded state wherein its pleats open up and form a generally continuous curved, e.g., cylindrical, inner and outer surface (as shown in FIG. 6). The inner surface forms a passageway P through the prosthesis through which blood will flow, as will be described later.

The anchoring stent means 26 comprises a pair of expandable tubular stents 34 and 36. Each stent is an expandable ring-like, member, like that disclosed in my aforementioned patent. One stent 34 is located at one end of the prosthesis 20, e.g., the end adjacent the renal arteries 14, while the other stent 36 is located at the other end of the prosthesis, e.g., the end adjacent the iliac bifurcation. In accordance with a preferred embodiment of this invention the stent 34 is fixedly secured to portions of the outside surface of the sleeve member 32 at one end thereof, while the stent 36 is fixedly secured to portions of the outside surface of the sleeve member 32 at the opposite end thereof. Each of the stents 34 and 36 includes anchoring means (to be described later) constructed in accordance with the teachings of my aforementioned copending patent application for anchoring the stents to the interior of the abdominal aorta 12 proximally and distally, respectively, of the aneurysm 10.

The intermediate support stent means 28 comprises a plurality of expandable tubular stents 38. Each stent 38 is an expandable ring-like member, like that disclosed in my aforementioned patent. The stents 38 are of slightly smaller outer diameter when expanded than the anchoring stents 34 and 36, and are located at equidistantly spaced positions within the sleeve member 32 between the anchoring stents 34 and 36. In accordance with a preferred embodiment of this invention the stents 38 are also each fixedly secured to portions of the outside surface of the sleeve member 32.

Figure 5:
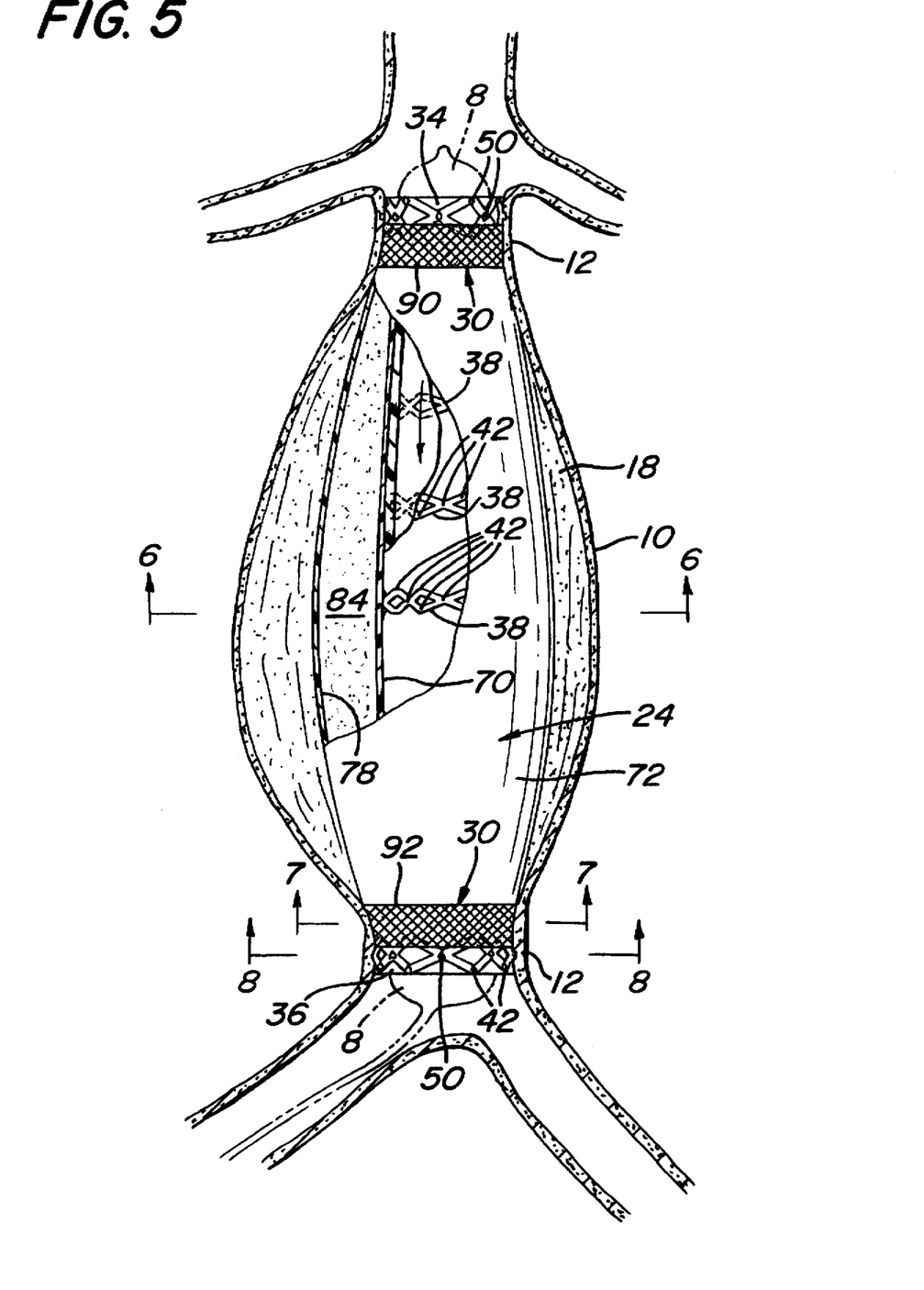
FIG. 5 is an illustration of the portion of the abdominal aorta shown in FIG. 1, with the prosthesis being in its expanded, fully operational state.

The anchoring stents 34 and 36 and the intermediate support stents 38 serve as a means for holding or retaining the sleeve member 32 in any desired expanded state (i.e., from the compact or compressed state shown in FIG. 1, to the fully expanded state like shown in FIG. 5). Thus, as can be seen, each of the stents 34, 36, and 38 basically comprises a plurality of interconnected links or struts 40. Each of the links is an elongated rigid member formed of stainless steel or some other suitable biocompatible material, e.g., tantalum, plastic. Each link 40 has a pair of ends and is joined to an associated link via a pivotable joint 42. Each joint 42 is made up of one end of one link and the other end of the immediately adjacent link. The link ends are connected by any suitable means, e.g., a deformable member, a pin, etc., to enable the links to pivot outward with respect to each other so that the angle therebetween increases, yet which precludes the links from pivoting backward-toward each other. In the embodiment shown herein the joint comprises the material making up the links themselves, and such material is deformable, but not resilient, so that once deformed, i.e., the links pivoted outward, it doesn't return to its previous configuration.

As should be appreciated by those skilled in the art when the links are pivoted outward with respect to each other the stents 34, 36, and 38 expand from their compact state to the expanded state. In accordance with a preferred aspect of this invention the joints at the interfaces of each of the links of the stents are arranged to maintain any angular orientation between the connected links from the compact state to the expanded state such that once the stents are expanded movement back to the compact state is precluded.

The links 40 of the stents 34, 36, and 38 of this invention serve to hold the sleeve member 32 in the expanded state. To that end, in the embodiment shown herein each of the stents is mounted on the outside of the sleeve member 32, whereupon the links 40 of those stents are connected to one or more pleats 32A externally of the sleeve member, i.e., on its outer surface. If desired, the stents could be disposed or mounted within the sleeve member 32. In the later case the links 40 can be connected internally of the sleeve. Moreover, if desired, the stents may be completely encased in the material forming the sleeve member.

In the preferred embodiment shown in FIG. 1, each of the stents 34, 36, and 38 is made up of pairs of interconnected links to form two zig-zag patterns sharing common joints, thereby creating a diamond-like pattern stent. Alternatively, the links may not be paired, so that a single zig-zag pattern is produced instead of the diamond-like pattern.

In order to-help hold or secure the graft in position in the artery (or lumen or duct) once the prosthesis has been expanded, the anchoring stents 34 and 36 include the heretofore mentioned anchoring means. Such anchoring means comprise plural protuberances or projections 50 (FIGS. 1, 4 and 10) which are mounted on those stents. In particular, each stent 34 and 36 includes a plurality of protuberances or projections 50 projecting slightly outward therefrom and from the outer surface of the sleeve member. As will be described in detail later, these projections 50 are preferentially oriented so that the force of the fluid, e.g., blood, flowing through the passageway P in prosthesis 20 when it is in place and expanded, is applied to them to cause them to tightly engage the interior of the wall making up the vessel, duct, or lumen. In particular, as will be described later with reference to FIG. 10, the projections 50 include portions extending at an acute angle to the direction which the fluid flows through the prosthesis when it is positioned intraluminally and opened, whereupon the force applied to the projections by that fluid flow includes a force component extending in the direction of the fluid flow and a force component extending radially, i.e., perpendicularly to the direction of the fluid flow. This action causes the projections to tightly engage, e.g., burrow slightly into, the interior of the vessel, duct, or lumen to fixedly secure the device in place.

It should be pointed out at this juncture the mechanism, e.g., pivot pin, deformable member, etc., forming each joint of the links making up the anchoring stents 34 and 36 may itself form a projection 50.

In the case of an interiorly located stent, i.e., a prosthesis wherein the anchoring stents 34 and 36 are located on the interior of the sleeve member 32 or embedded within the material making up the sleeve (as discussed earlier), the projections 50 must extend through the sleeve member so as to be located on the outer surface of the sleeve. Another suitable arrangement for a device using an interiorly located stent is to utilize projections which are not part of the stent itself.

Figure 10:
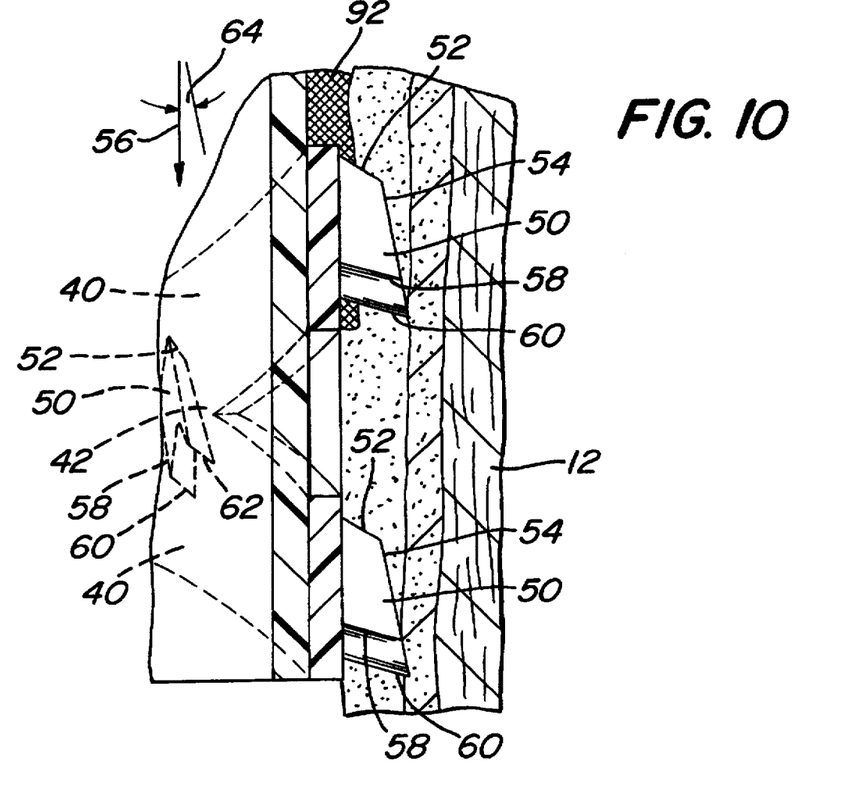
FIG. 10 is a greatly enlarged sectional view taken along line 10—10 of FIG. 8.

Referring now to FIGS. 10, the details of the projections 50 will now be described. As can be seen therein each projection is of a generally "arrow head" shape when viewed in plan. In particular, each projection includes a leading edge 52 defining the "tip" of the "arrow-head." The leading edge 52 extends upward at an acute angle to the exterior surface of the stent and terminates at the top surface 44 of the projection. The top surface 54 is generally planar and inclines upward in the direction of blood flow. That direction is designated by the arrow 56 in FIGS. 1, 5 and 10. The trailing edges of each projection are designated by the reference numbers 58, 60, and 62, and each inclines upward in the direction of the blood flow to terminate at the top surface 54 in respective penetration points. Thus, as can be appreciated each of the projections 50 includes portions which are preferentially oriented at an acute angle to the direction of blood flow. The acute angle is shown in FIG. 10 and designated by the reference numeral 64.

As will be appreciated by those skilled in the art, with blood (or some other fluid) flowing through the passageway P in the prosthesis in the direction of arrow 56 a force will be applied by that flow to the interior surface of the sleeve member 32, and from there through the anchoring stents 34 and 36 to the projections thereon. The force applied to those projections will have a force component directed in the direction of the fluid flow, and a force component perpendicularly thereto, i.e., extending radially outward. Thus, the flow of fluid, e.g., blood, through the passageway in the sleeve member 32 will tend to force the projections 50 into good engagement with the wall 12 of the vessel, duct, or lumen. In the embodiment shown herein the projections penetrate or burrow slightly into the artery wall, as shown clearly in FIG. 10. Such penetration may not be necessary for good resistance to migration of the prosthesis. If some penetration is deemed desirable the height of the projections is selected so that their penetrating points do not penetrate too deeply into the artery wall. In this regard, the height of the projections is selected so that they do not penetrate into the medial or adventitial layers of the artery wall, but can penetrate its intima. It is anticipated that for applications within the very largest arteries, such as the abdominal aorta, that the height of the projections will be in the range of approximately 1.0 mm to 1.5 mm.

As should be appreciated by those skilled in the art the number of projections 50 used in any prosthesis will also be a considerable a factor in the amount of securement against migration provided thereby. Thus, as a general proposition, the more projections utilized the less "penetration" or "burrowing" will necessary for good securement against migration.

It should be pointed out that anchoring projections constructed accordance with my aforementioned invention can take numerous other shapes and sizes than those shown herein. In this regard, the projections need not include sharp edges and/or planar surfaces or points. Thus, they can be rounded, domed, or any other suitable shape, so long as they are preferentially oriented to project or extend at some acute angle to the direction of fluid flow, whereupon the force applied to them by the fluid flowing through the vessel, duct, or lumen, produces on each of them a force component extending in the direction of the fluid flow and a force component extending perpendicularly to that direction. As discussed above this action causes the projections to tightly engage (and not necessarily penetrate) the interior of the wall of the vessel, duct, or lumen to fixedly secure the prosthesis in place against migration.

Referring now to FIGS. 1, 2, 5, 6, and 9 the details of the outer balloon means 24 will now be considered. To that end the outer balloon means basically comprises an annular member having a cylindrical inner wall 70, a generally cylindrical outer wall 72, and interconnecting end wall portions 74 and 76 (FIG. 9) defining a hollow space 78 (FIGS. 5 and 9) therebetween. The balloon is an integral unit, preferably formed of a very flexible material, such as that typically used in conventional balloon catheters. The material making up the balloon may be stretchable, if desired. The inner surface of the inner wall 70 of the balloon is fixedly secured by any suitable means, e.g., an adhesive (not shown), to the outer surface of the sleeve member 32 and the outer surface of the intermediate support stents 38 between the pair of anchoring stents 34 and 36. An self-sealing port 80 (FIG. 9) is provided in the balloon for communication with a tube or conduit 82 extending from outside the body of the patient. The conduit 82 is arranged to carry a fluid, e.g., a gel or saline solution 84 (FIG. 5), therethrough for introduction through the port 80 into the interior 78 of the balloon to inflate the balloon. Preferably the balloons interior 78 is filled sufficiently to cause the outer wall of the balloon to extend outward to completely fill the aneurysmal space longitudinally, but only to partially fill the aneurysmal space transversely so that an excess force is not produced radially which could dislodge the aneurysm thrombus. This action causes respective portions of the outer surface of the outer wall 72 to engage the surface of the thrombus 18 and the inner surface of the abdominal aorta 12 on proximal and distal sides of the thrombus. Accordingly, the thrombus is trapped between the outer wall of the balloon and the inside surface of the artery wall. Once the balloon has been expanded sufficiently to seal the aneurysmal space, as just described, the conduit 80 can be removed, whereupon the self-sealing port 80 closes to trap the fluid 84 within the balloon, thereby keeping the balloon inflated. The inflation of the balloon with the fluid 84 effects the stiffening of the prosthesis 20, thereby rendering it resistant to migration. If desired the fluid may be a "settable" fluid or gel to further stiffen the prosthesis, although this should not be necessary since the balloon will tend to maintain its rigidity due to the tension on its outer wall caused by the fluid therein even if in liquid or gel form.

In the interests of providing a prosthesis which when in its compressed or compact state is of very small diameter, the outer wall 72 of the balloon is preferably thinner than the inner wall 70 of the balloon. Such a construction will enable the larger outer wall to take up less space than if it were of the same thickness as the inner wall.

As should be appreciated by those skilled in the art the expansion of the balloon, as just described, effectively sets or secures the prosthesis 20 in place, thereby aiding in the securement provided by the anchoring stents 34 and 36.

Figure 4:
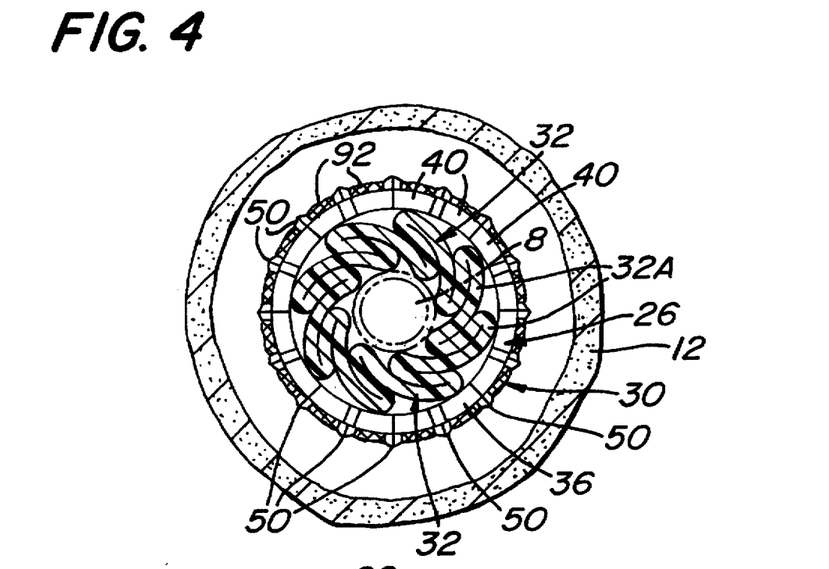
FIG. 4 is an enlarged sectional view taken along line 4—4 of FIG. 1.

In order to seal the aneurysmal space, i.e., to prevent any blood from flowing into the aneurysmal space between the outer surface of the outer balloon and the inner surface of the artery at the proximal end of prosthesis, and for precluding the egress of any emboli out of that aneurysmal space from the distal end of the prosthesis, the heretofore identified sealing means 30 are provided. Such means is best seen in FIGS. 4, 5 and 10 and basically comprises a pair of sealing rings 90 and 92. Each of the sealing rings is formed of any suitable material, e.g., mesh, foam, etc., which forms a hemostatic seal, e.g., promotes hemostasis, between the prosthesis and the arterial wall. As should be appreciated by those skilled in the art when mesh is used for the sealing means it may be formed of either loosely organized or loosely disorganized fibers in order to expedite and promote hemostasis. Preferably the mesh is formed of a material which is thrombogenic and fibrogenic, the latter feature promoting or stimulating the incorporation of the ends of the prosthesis by fibrosis to the interior of the artery wall.

Figure 8:
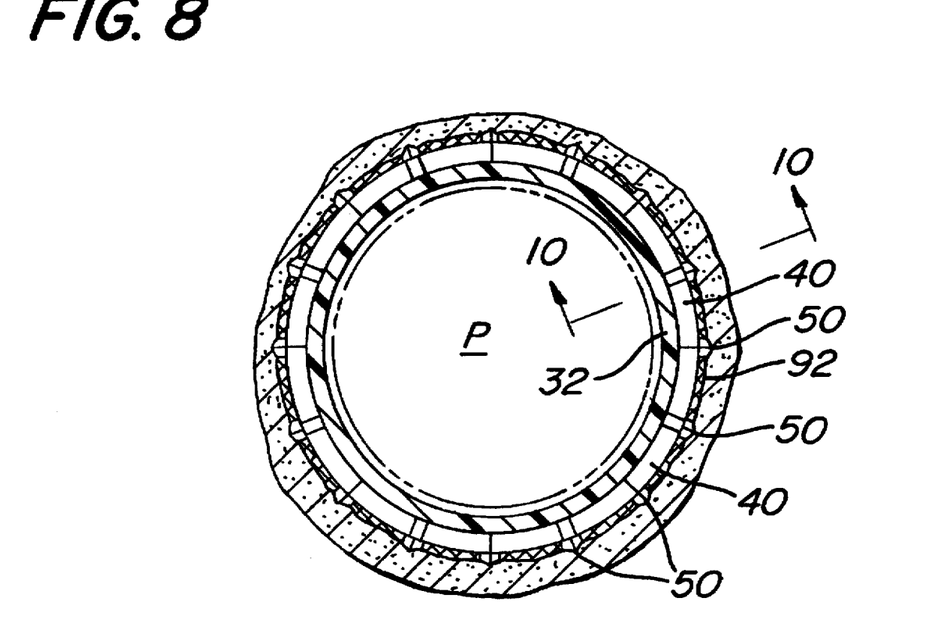
FIG. 8 is an enlarged sectional view taken along line 8—8 of FIG. 5.
Figure 9:
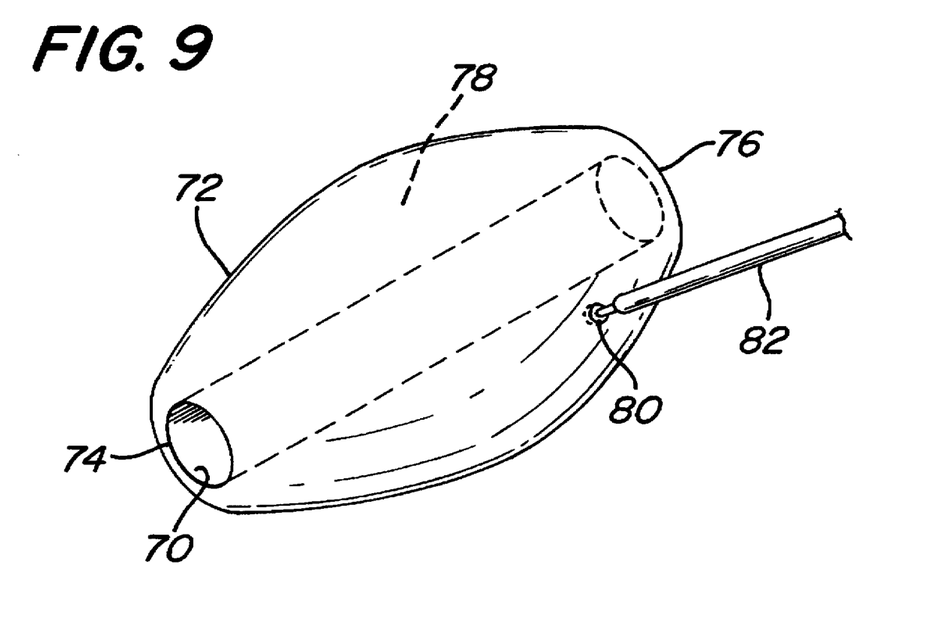
FIG. 9 is an enlarged isometric view of a portion of the prosthesis shown in FIG. 1.

Each sealing ring is also expandable so that when the prosthesis is expanded, each sealing ring expands with it. The sealing rings 90 and 92 are located so that portions thereof overlie and are secured to portions of the anchoring stents 34 and 36, respectively, with the locking protuberances 50 extending through the sealing rings to engage the inner surface of the artery wall as shown clearly in FIGS. 8 and 10.

When the prosthesis 20 is in place and expanded like shown in FIG. 5, the sealing rings 90 and 92 are interposed between the outer surface of the prosthesis and the inner wall of the abdominal aorta on opposite sides of the aneurysm, i.e., proximally and distally. This action effectively blocks the ingress of blood into the aneurysmal space and the egress of emboli therefrom.

The following constitutes the methodology for placing the prosthesis 20 of the subject invention the abdominal aortic aneurysm 10. To that end the prosthesis in its compact state is crimped over an introducing instrument, e.g., a conventional balloon catheter 8, so that the instrument extends through the compacted passageway P in the sleeve member 32. The prosthesis 20 on the introducing instrument is then introduced into the aneurysm 10 through a sheath (not shown), usually at some distance from the aneurysm, e.g., a percutaneous puncture in the femoral artery, and threaded over a conventional guide wire (not shown) into place. The sleeve member 32 and the anchoring stents 34 and 36 and intermediate support stents 38 are then expanded as a unit to a partially expanded state, i.e., a state slightly smaller than the prosthesis fully expanded state shown in FIG. 5. The expanding instrument, e.g., the balloon catheter 8, is left in place within the partially expanded prosthesis. The outer balloon 24 is then inflated by introducing the inflation fluid 84 into it via the conduit 82 and associated self-sealing port 80. The partially expanded stents 34, 36 and 38 prevent the radially inward collapse of the inner wall 70 of the balloon 24 during and after inflation.

After the outer balloon 24 is filled sufficiently to create the desired rigidity, and a good seal at both ends, the conduit 82 is removed, thereby causing the self-sealing port 80 to seal shut. This action entraps the inflation fluid 84 within the outer balloon to maintain its rigidity. The introducing balloon catheter 8 is then operated (inflated) to complete the expansion of the sleeve member 32 and associated stents 34, 36 and 38 (i.e., to expand them to their fully expanded state). This action causes the outer surface of the outer wall 72 of the balloon 24 to engage and compress the thrombus 18 within the aneurysmal space, while the anchoring stents move into very close proximity to the contiguous inner surfaces of the arterial wall 12 so that their locking protuberances 50 tightly engage those surfaces. The balloon 8 is then withdrawn from the passageway P through the sleeve member by deflating the balloon and then pulling it out of the prosthesis.

Blood is then able to flow through the passageway P in the prosthesis in the direction of arrow 56, with the sealing member 90 preventing any ingress of blood into the aneurysmal space between the outer wall of the prosthesis and the inner surface of the artery at the proximal end of the aneurysmal. The sealing member 92 prevents the egress of any emboli from that aneurysmal space at the distal end. The blood flowing through the passageway P in the prosthesis applies a force to the protuberances 50 to cause them to more tightly engage, e.g., burrow slightly, into the arterial wall, to thereby lock the prosthesis in place against migration.

As will be appreciated by those skilled in the art during the placement procedure, arteriography is necessary to ensure that there is proper placement of the prosthesis and that there is no leakage around the proximal or distal ends of the prosthesis prior to removal of the introducing instrument, e.g., the balloon catheter. If there is any such leakage, the balloon catheter can be expanded further to effect a good seal between the prosthesis 20 and the arterial wall.

It should be pointed out at this juncture that separate means may not be necessary to effect the expansion of the prosthesis when in position within the aneurysmal space. In this regard, the stents forming a portion of the device may be constructed to be self-expanding. Moreover, for some applications anchoring stents and/or support stents may not be required since the expanded outer balloon may provide sufficient rigidity to prevent migration of the prosthesis from its placed position. Further still, sealing members may not be required in some applications if the interface between the outer surface of the outer balloon and the inner surface of the artery wall on the proximal and distal sides of the aneurysm are sufficiently tight and sealed to prevent the ingress of blood therethrough and the egress of emboli thereout. Further yet, the inner wall of the outer balloon may, itself, serve as the sleeve through which blood will flow, thereby eliminating the need for a separate sleeve member.

In some applications additional sealing means, e.g., a sealing mesh covering (to be described hereinafter), extending over substantially the entire exterior surface of the outer balloon may be desirable to ensure that a complete seal is formed between the prosthesis and the interior of the artery wall. Moreover, such a covering should result in the occlusion of collateral branches to the aortic aneurysm, e.g., the inferior mesenteric artery and the lumbar arteries, thereby preventing a source of further aneurysm growth and expansion and its attendant risk of rupture. prosthesis 20 having the alternative sealing covering is shown clearly in FIGS. 11–14. It must be pointed out at this juncture that the prosthesis 20' of this alternative embodiment is in all respects the same as the embodiment 20 described heretofore, except for the use of a sealing means covering in lieu of the two sealing rings 30. Thus, in the interest of brevity the common components of the alternative embodiment 20' of FIGS. 11–14 and the previously described embodiment 20' of FIGS. 1-10 will be given the same reference numbers and their structure and operation will not be reiterated. It should be noted that in the interests of drawing simplicity the sleeve means 22 has been omitted from FIG. 11, and the anchoring stents 26 have been omitted from FIG. 14.

Figure 11:
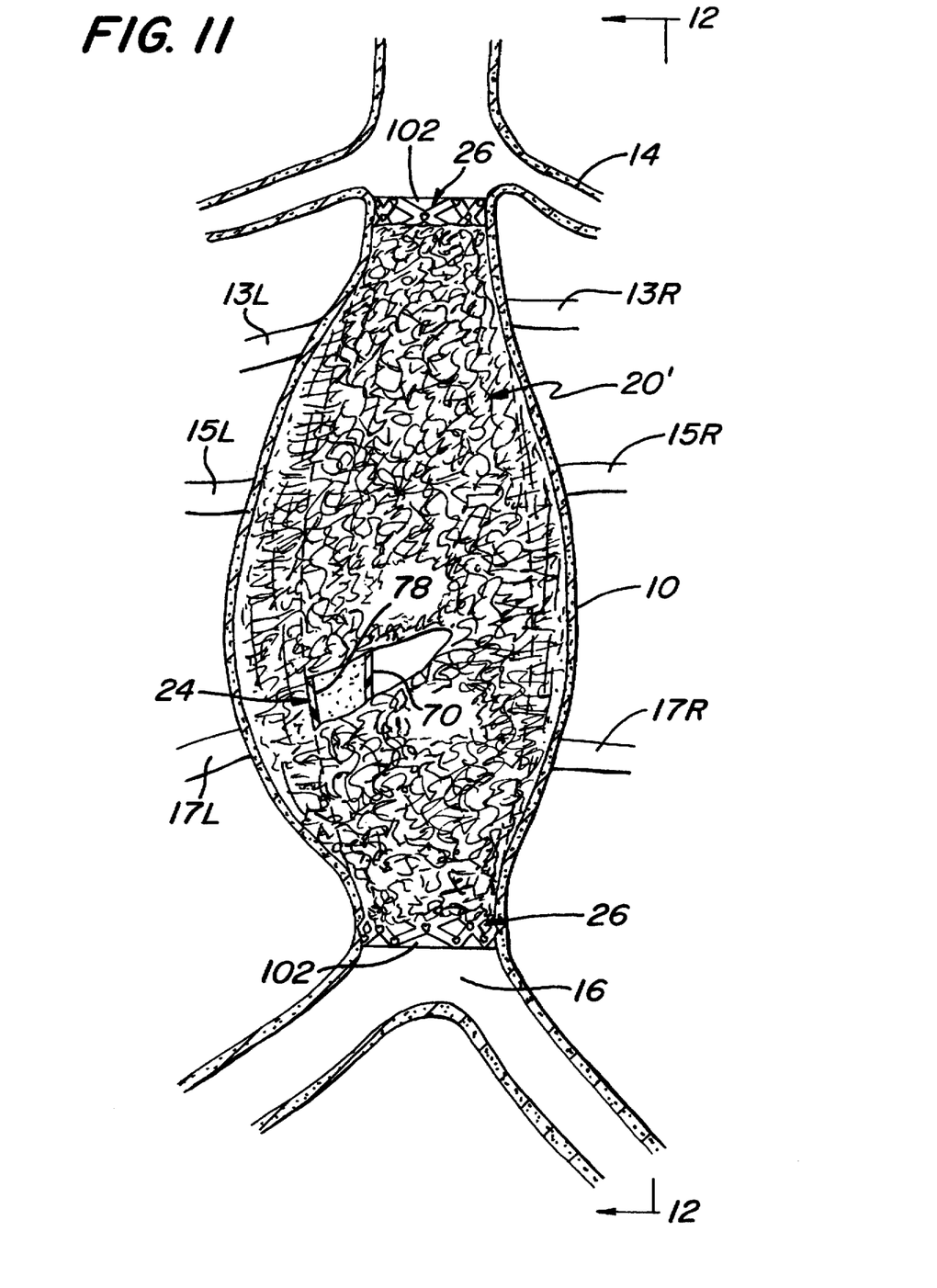
FIG. 11 is a front plan view illustration, like that of FIG. 1, but showing more of the vascular system contiguous with the portion of the abdominal aorta, and showing an alternative embodiment of the prosthesis of the subject invention in partial section located therein, with the prosthesis being in its expanded, fully operational state.
Figure 13:
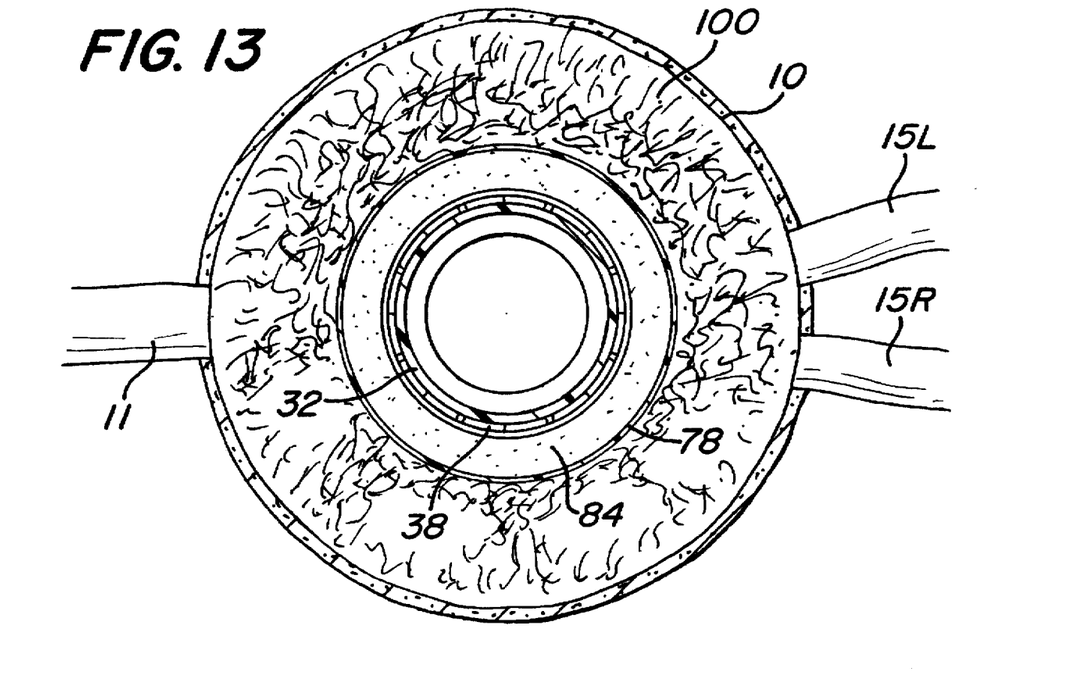
FIG. 13 is an enlarged sectional view taken along line 13—13 of FIG. 12.
Figure 14:
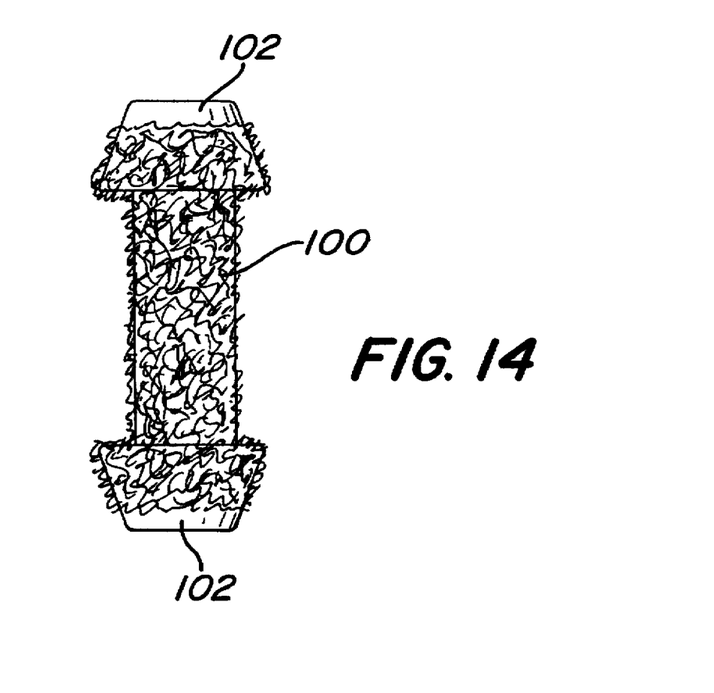
FIG. 14 is a top plan view of the embodiment of the prosthesis shown in FIG. 11 showing one preferred manner of differentially expanding the prosthesis to the expanded, fully operative state.

As can be seen clearly in FIGS. 11 and 14 the prosthesis 20' includes a sealing covering 100 disposed over and secured to the outer surface of the outer wall 72 of the balloon 24, except for a pair of cuffs 102 (FIG. 14) located at the ends of the balloon at which the stents 26 are located. The covering 100 may be formed of either loosely organized or loosely disorganized fibers in order to expedite and promote hemostasis. In the embodiment shown in FIGS. 11–14 the fibers are loosely disorganized, and like the sealing means described earlier are preferably formed of a material, e.g., dacron, which is thrombogenic and fibrogenic. Thus, when the prosthesis is located within the aneurysm in the abdominal aorta and fully expanded to the operative state as shown in FIG. 11, the covering 100 will engage the inner surface of the artery wall adjacent each end of the prosthesis to seal it as described earlier, while the fibrillar fibers of the covering 100 are compacted into the aneurysmal aortic thrombus to intermingle with the thrombus and thereby lock the prosthesis in place. Moreover, the fibrillar fibers of the covering mesh 100 tend to seal the junctures of the abdominal aorta to the origins of its collateral branch arteries, e.g., the inferior mesenteric artery 11 (FIG. 13) and the lumbar arteries 13L and 13R, 15L and 15R, and 17L and 17R, so that blood cannot gain ingress into the aneurysmal space from these arteries, which action could result in aneurysm growth and concomitant risk of rupture. Further still, since the mesh covering is thrombogenic and fibrogenic it stimulates the incorporation of the prosthesis 20' by fibrosis to the aortic wall, thus ensuring a complete and permanent seal. Thus, the prosthesis 20' prevents further aortic aneurysm expansion and rupture by also strengthening the aortic wall due to fibrosis.

The cuffs 102 of the prosthesis are preferably devoid of the covering mesh 100 in order to prevent the protrusion of the mesh into the origins of the renal arteries above the prosthesis and the protrusion of the mesh into the origins of the iliac arteries below the prosthesis.

Figure 12:
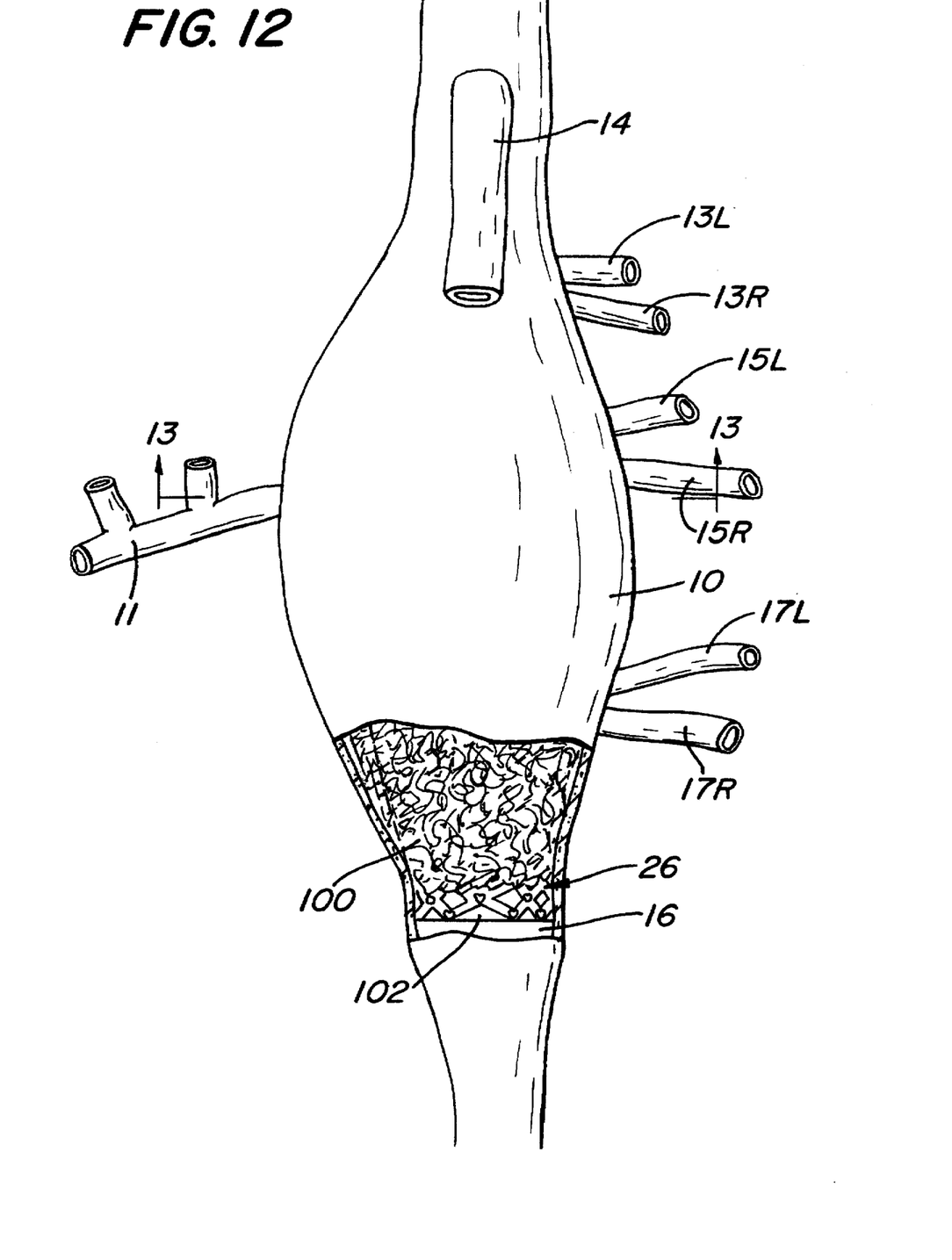
FIG. 12 is a side elevational view illustration taken along line 12—12 of FIG. 11.

In accordance with one preferred aspect of this invention the prosthesis 20' is arranged to be differentially expanded, i.e., the portion thereof adjacent either end of the prosthesis expanded first, followed by the expansion of the other end, as shown in FIG. 14. The middle portion of the prosthesis can be expanded. This differential expansion ensures that the aneurysmal intraluminal thrombus is trapped in position by the expanded ends of the prosthesis before the intermediate or middle portion of the prosthesis is expanded to complete the expansion of the prosthesis to its fully expanded, operative state such as shown in FIGS. 11–13.

Without further elaboration the foregoing will so fully illustrate my invention that others may, by applying current or future knowledge, adopt the same for use under various conditions of service.

I claim:

1. An intraluminal prosthesis for introduction within a portion of a blood vessel, duct or lumen of a living being having an aneurysm in the wall thereof defining an aneurysmal space, the wall of the portion of the vessel, duct, or lumen having an interior surface, said prosthesis comprising a sleeve, an outer balloon, and sealing means for sealing said prosthesis to portions of the vessel, duct or lumen, said sleeve comprising an elongated tube having a passageway therethrough, a longitudinal axis, and a pair of ends, said passageway being arranged to convey fluid therethrough, said outer balloon being disposed about said sleeve and arranged to be filled with a filling material to cause an outer surface of said outer balloon to extend outward to engage the aneurysm in the wall of the vessel, duct or lumen and to substantially completely fill the aneurysmal space within the vessel, duct, or lumen, said sealing means being formed of a loose fibrillar material which stimulates hemostasis and fibrous tissue ingrowth and being disposed about said outer surface of said outer balloon to cover most of said outer surface, said prosthesis being arranged to be fixedly secured to the interior of the vessel, duct, or lumen with said ends of said sleeve means capable of being sealed to portions of the vessel, duct or lumen on respective sides of the aneurysm by said sealing means, whereupon said sealing means precludes the ingress of fluid between the outer balloon and the interior of the vessel, duct or lumen at the situs of the aneurysm, while enabling fluid to be conveyed through said passageway, and to preclude the egress of material from between said outer balloon and the interior of the vessel, duct or lumen at the situs of the aneurysm.

2. The prosthesis of claim 1 wherein said sealing means comprises a mesh-like material.

3. The prosthesis of claim 2 wherein said mesh-like material is of loosely arranged fibers.

4. The prosthesis of claim 3 wherein said loosely arranged fibers are disorganized.

5. The prosthesis of claim 3 wherein said loosely arranged fibers are organized.

6. The prosthesis of claim 1 wherein at least one collateral branch is in fluid communication with the aneurysmal space and through which fluid tends to leak into the aneurysmal space, and wherein said sealing means is arranged to reduce or preclude the leakage of the fluid into the aneurysmal space from the at least one collateral branch.

7. The prosthesis of claim 1 wherein said outer balloon includes an opposed pair of end portions and wherein said sealing means covers said outer surface of said outer balloon except for said opposed portions.

8. The prosthesis of claim 7 wherein said sealing means comprises a cover secured to said outer surface of said outer balloon.

9. The prosthesis of claim 1 wherein said sleeve is arranged to be expanded to an expanded state when in position within the portion of the vessel, duct, or lumen to cause said passageway to be enlarged, and whereupon once said sleeve is expanded to said expanded state it remains in said expanded state.

10. The prosthesis of claim 1 additionally comprising anchoring means located adjacent each of said ends of said sleeve for anchoring said prosthesis to contiguous portions of the wall of said vessel, duct, or lumen.

11. The prosthesis of claim 10 wherein said anchoring means comprises at least one expandable stent.

12. The prosthesis of claim 9 additionally comprising an expandable stent for effecting the expansion of said sleeve to said expanded state, and for maintaining said sleeve in said expanded state.

13. The prosthesis of claim 1 wherein said sleeve is formed of a first relatively flexible material to enable said prosthesis to bend longitudinally with respect to said axis for ready placement within a curved vessel, duct, or lumen.

* * * * *